United States Patent [19]
de Zoeten et al.

[11] Patent Number: 5,611,995
[45] Date of Patent: Mar. 18, 1997

[54] APPARATUS FOR THE DETECTION OF A SPECIFICALLY REACTING SUBSTANCE

[75] Inventors: Juan P. de Zoeten, Boxtel; Petrus F. H. M. Verheijden, Eersel; Theodorus J. J. Groothuizen, Rotterdam; Jozef H. M. Raijmakers, Delft, all of Netherlands

[73] Assignee: Akzo Nobel N.V., Arnhem, Netherlands

[21] Appl. No.: 454,352

[22] PCT Filed: Mar. 16, 1994

[86] PCT No.: PCT/EP94/00899

§ 371 Date: Jun. 6, 1995

§ 102(e) Date: Jun. 6, 1995

[87] PCT Pub. No.: WO94/22011

PCT Pub. Date: Sep. 29, 1994

[30] Foreign Application Priority Data

Mar. 17, 1993 [DE] Germany .................. 43 08 521.0

[51] Int. Cl.$^6$ .................................................. G01N 31/22
[52] U.S. Cl. .......................... 422/58; 422/61; 436/65; 436/814
[58] Field of Search ........................ 422/56, 58, 61, 422/101, 102; 436/65, 814

[56] References Cited

U.S. PATENT DOCUMENTS

| | | | |
|---|---|---|---|
| 4,696,797 | 9/1987 | Kelton | 422/58 |
| 4,808,379 | 2/1989 | Wardlaw et al. | 422/58 |
| 4,952,373 | 8/1990 | Sugarman et al. | 422/58 |
| 5,084,248 | 1/1992 | Berke et al. | 422/61 |
| 5,281,395 | 1/1994 | Markart et al. | 422/58 |

FOREIGN PATENT DOCUMENTS

| | | |
|---|---|---|
| 0183442 | 6/1986 | European Pat. Off. |
| 0291194 | 11/1988 | European Pat. Off. |
| 0314328 | 5/1989 | European Pat. Off. |
| WOA9311434 | 6/1993 | WIPO |

*Primary Examiner*—Lyle A. Alexander
*Attorney, Agent, or Firm*—Gregory R. Muir

[57] ABSTRACT

An apparatus detects a specifically reacting substance in a test liquid. The apparatus has a housing and a holding device thereon for holding a test strip. The test strip has a material that transports a test liquid essentially by capillary forces and has an analytical system which indicates the presence or absence of the substance to be detected. The holding device can be attached to the housing with an opening therebetween for allowing evaporation of test liquid. The housing can be elongated for accepting a sample collector therein. A contact mechanism can also be disposed for promoting contact of liquid sample from the sample collector when inserted in the housing, to the test strip held by the holding device.

12 Claims, 8 Drawing Sheets

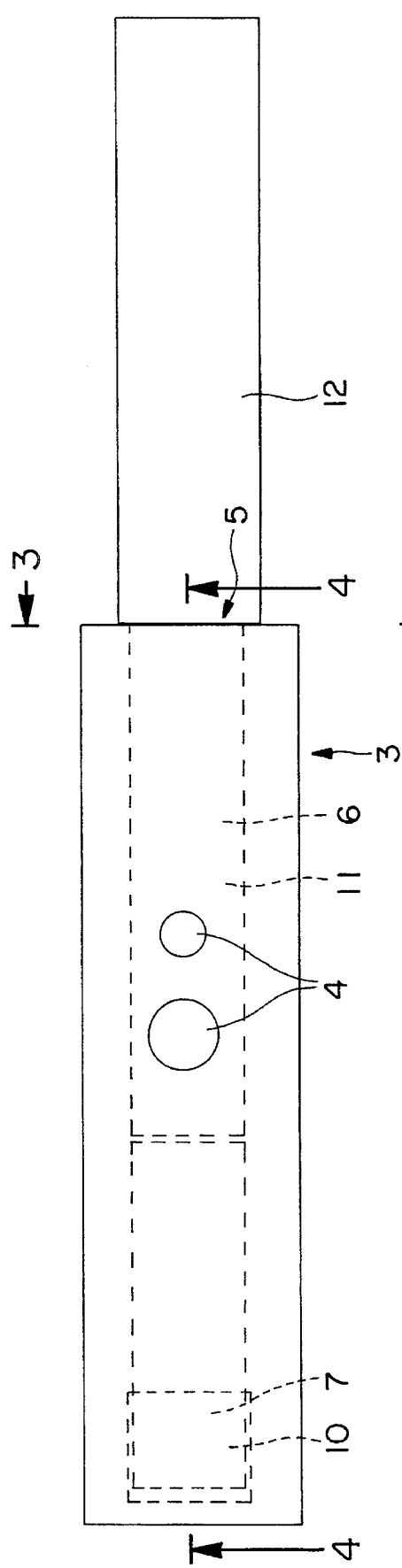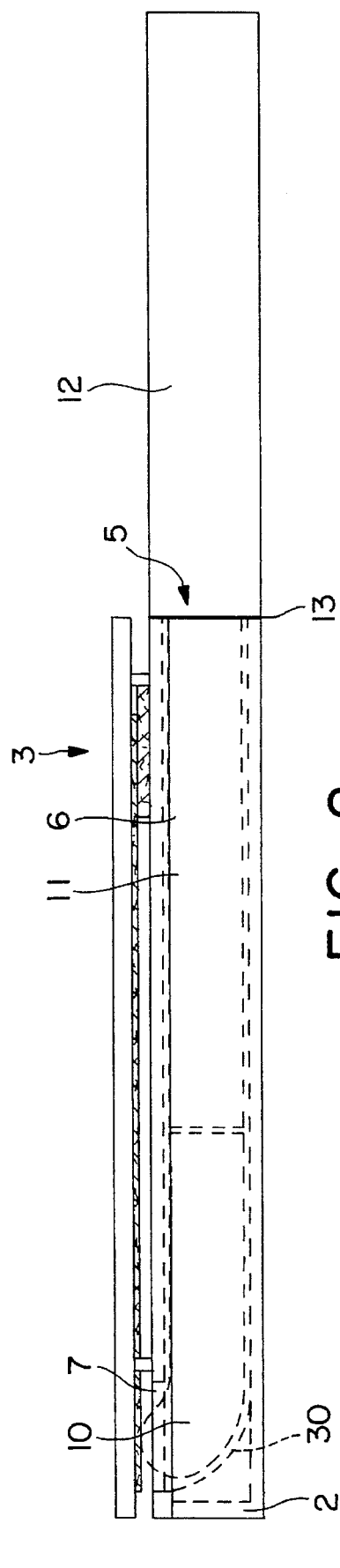
FIG. 1
FIG. 2

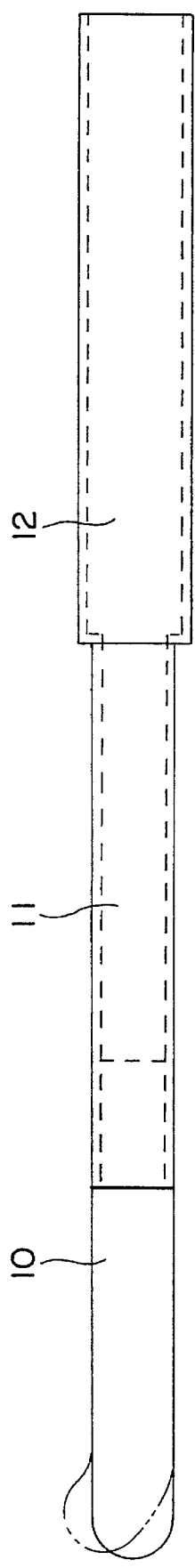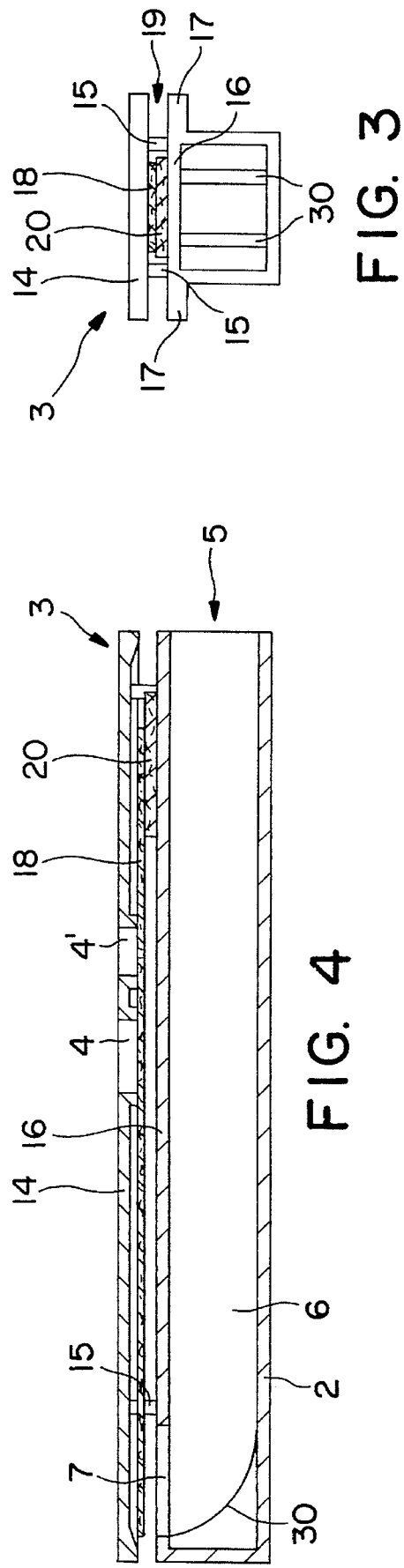

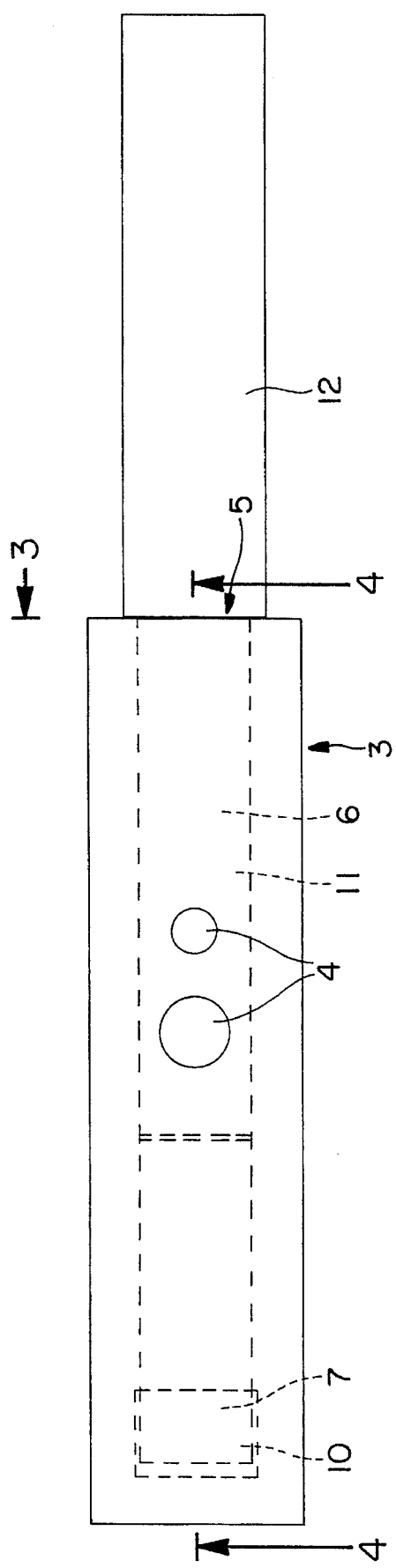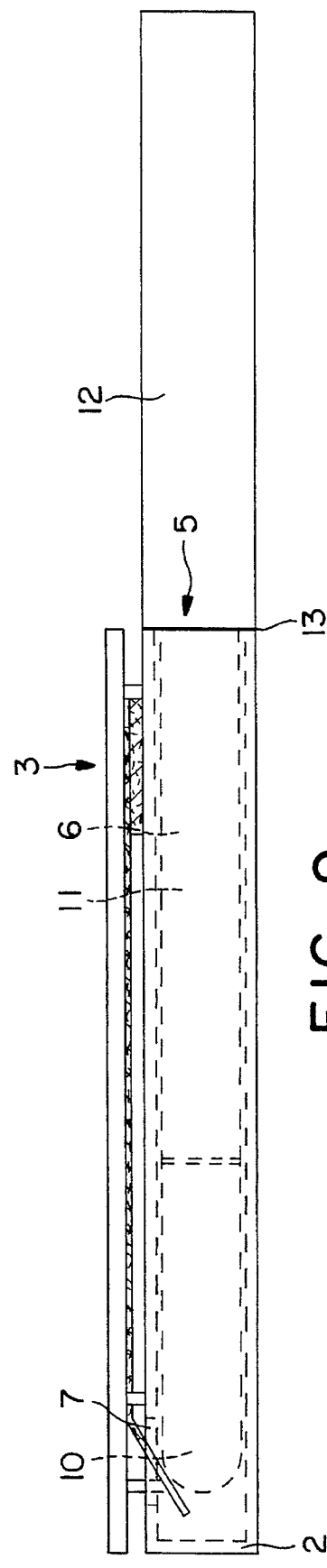

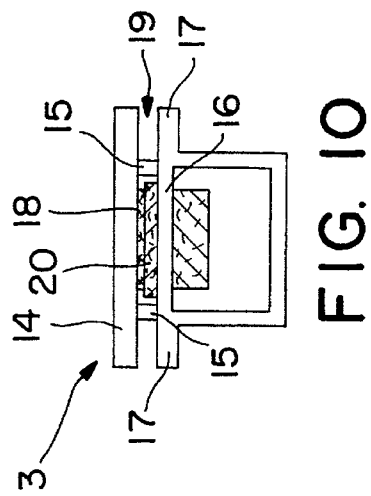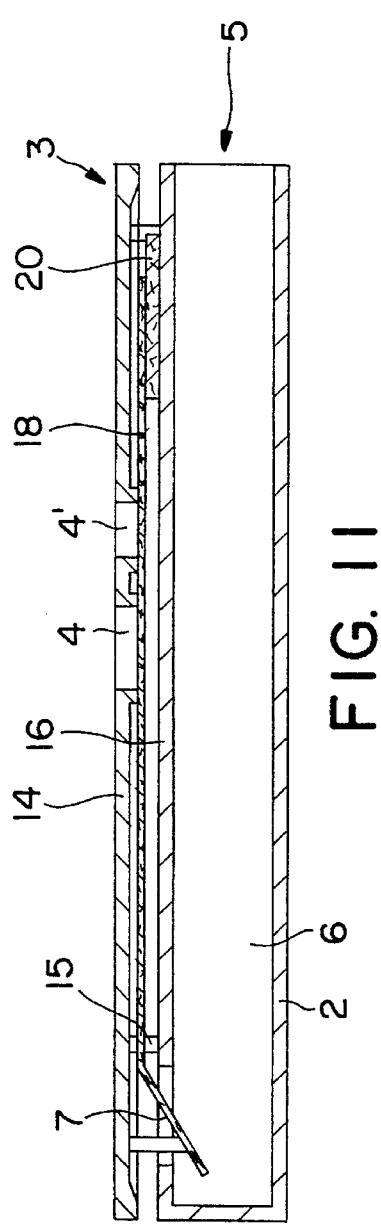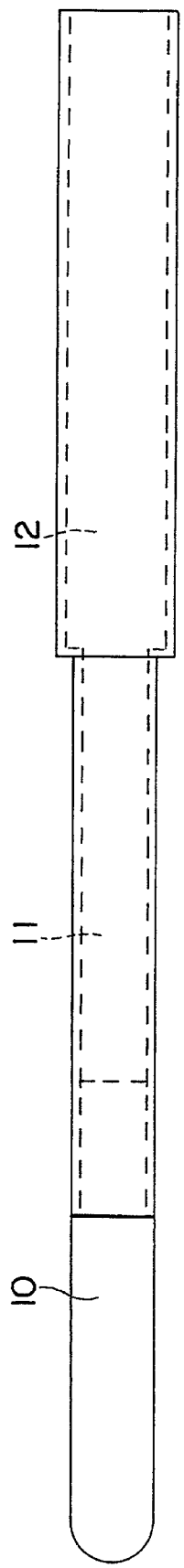

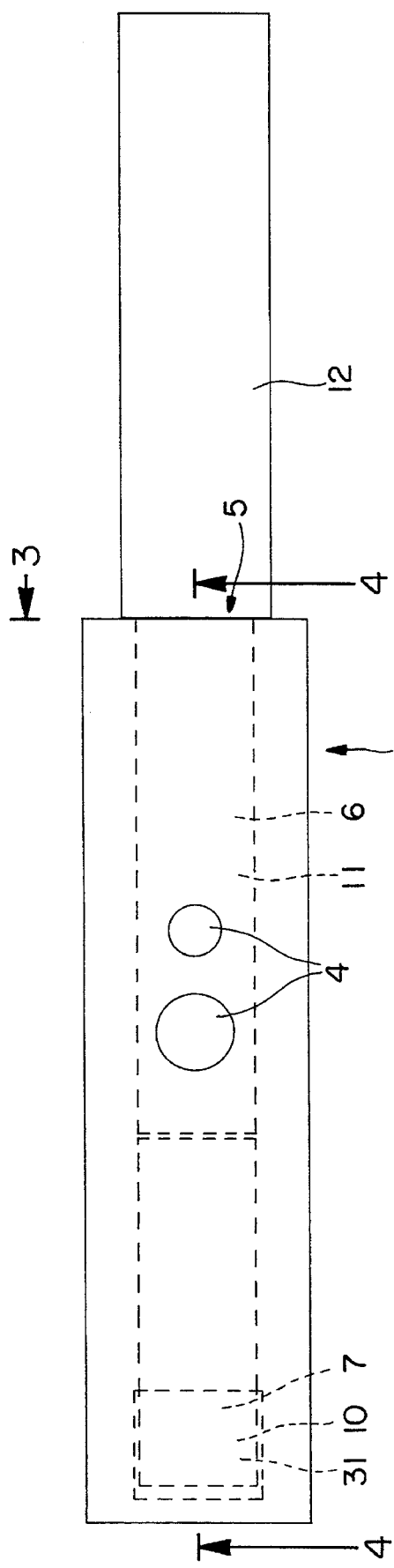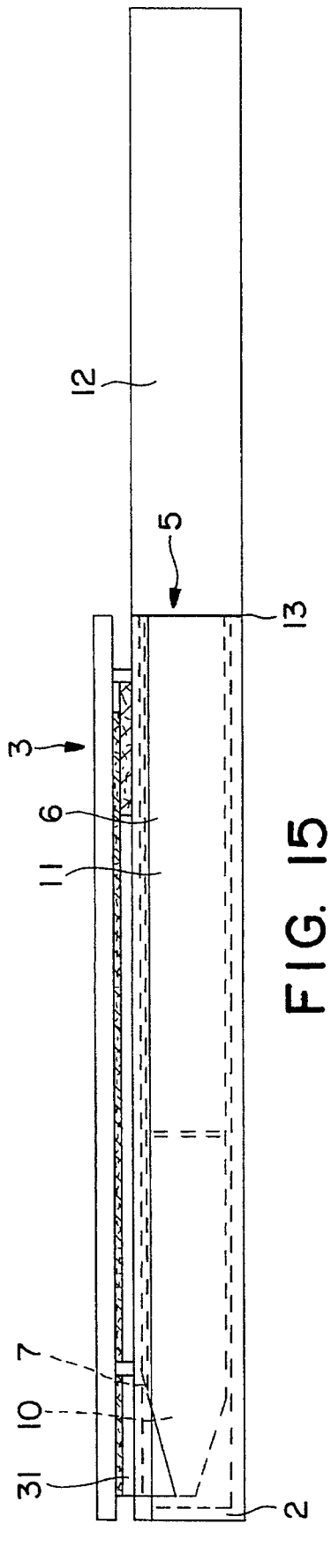

APPARATUS FOR THE DETECTION OF A SPECIFICALLY REACTING SUBSTANCE

BACKGROUND OF THE INVENTION

1. Field of the Invention

The invention relates to an apparatus for the detection of a specifically reacting substance in a test liquid. In this apparatus a test strip is involved comprising an analytical system. The apparatus of the invention is specifically intended for home use or use by nonprofessional organisations, whereby the test is usually carried out by laymen or non skilled people.

In the state of the art there are various types of test strips for detecting specifically reacting substances. Such a test strip can for example, when provided with a certain colour indicator, be used for measurement of the pH of the test liquid. However, for the detection of specifically reacting substances by an immunoassay, test strips with a more complicated analytical system are required. Upon contact with such a test strip, which is preferably made of a porous material, the test liquid, possibly containing the specifically reacting substance to be detected, is transported along the test strip by capillary action. The test strip usually contains different reagent zones comprising for example specific reactants for the substance to be detected. One of these reactants is provided with a label, preferably a coloured label which can be observed visually. The test liquid subsequently passes the various reagent zones, whereby different immunological reactions will take place. The complexes formed will finally be bound by a reagent on the detection spot and will be visible by the label involved. Such strips are now commercially available.

2. Description of the Related Art

EP-A-0 183 442 discloses a chromatographic device comprising a housing and a strip of bibulous material non-removably confined in the housing. The inner walls of the housing contain means for supportively confining the strip in the housing. This means supportively confines the strip in the housing so that the front and back of the strip are essentially free from contact with the walls of the housing. The bottom end of the housing contains means for enabling a portion of the strip to contact the liquid medium. The housing additionally contains means for visually observing the strip.

EP-A-291 194 discloses an analytical test device which consists of a hollow casing of rigid material which is impermeable to moisture, and contains in the casing a dry porous support. The support is connected to the outside of the casing in such a way that a liquid test sample can be applied to the support. The sample then migrates through the support, on which immunological reactions take place and provide a visible analytical result in a particular zone of the support. In order to be able to observe the latter, openings are also provided in the casing. Direct labelling materials such as, for example, gold sol particles are used for visualization.

EP-A-0 349 215 discloses a test cell for detection of a ligand in a liquid sample, comprising an elongate casing for a permeable material. This permeable material is capable of transporting an aqueous solution disposed within the casing and comprises a receptor for the ligand. Receptor-coupled coloured particles are used for detection of the ligand. Observation of the test site is permitted by a hole or transparant section of the casing.

The known apparatuses for the detection of specifically reacting substances comprise a test strip, with an analytical system, enclosed in a housing. This housing is almost hermetically sealed, so that, after reaction of the test liquid with the reagents on the test strip, evaporation of the test liquid is seriously delayed or even prohibited. As a consequence the reagents may diffuse back to the detection spot, which will give rise to incorrect results.

SUMMARY OF THE INVENTION

The present invention is concerned with the improvement of the known techniques, such as those referred to in the above publications, especially with regard to the reliability of the test results. These improvements have been achieved with an apparatus for the detection of at least one specifically reacting substance in a test liquid comprising
— a housing
— a holding device and
— a test strip which is held in the holding device and which consists of a material that transports the test liquid essentially by capillary forces and comprises an analytical system which indicates the presence or absence of said substance to be detected, preferably by a colour,
whereby
— the housing has an interior space and opening for introducing said test liquid into said interior space and optionally means via which contact of the test liquid with the test strip can take place;
and
— the holding device comprises a base and a cover, said holding device being substantially open on its longitudinal and/or tranverse sides and said holding device being provided with at least one window for observing the test result, prefarably a colour.

The important aspect of the apparatus according to the present invention is that it contains a separate holding device (for a test strip) which is substantially open, in addition to and separate from a housing that is solely designed for receiving and transferring the test liquid.

The housing is advantageously produced from a material which is impermeable to moisture, such as thermoplastic material, polystyrene or the like, and acts to receive and transfer a certain amount of the test liquid. For this purpose the housing is equipped with an interior space and an opening for introduction of the test liquid and optionally means via which contact of the test liquid with the test strip can take place.

The test liquid can directly be introduced into the housing, for example with a pipette, or indirectly with a separate sample collector, the latter obviously being preferred. When the test liquid is introduced directly, the housing is preferably provided with visible calibrations, to control the correct volume of test fluid required for detection of the specifically reacting substance. The housing may also contain a filter to remove possibly interfering substances from the test liquid.

In order to allow contact between the test liquid and the test strip the housing optionally contains means via which this contact can take place. These means are preferably a (second) opening, which can have a round or square form or a split.

The holding device is advantageously made from the same material as the housing. Its main function is to hold the test strip with the analytical system in a special way. The holding device consists of a base and a cover, whereby the longitudinal and/or transverse sides are designed substantially open to ensure an adequate and quick drying of the test strip after reaction with the test liquid. In this way the so-called "back-diffusion" of the reagents, which leads to incorrect results, is eliminated. When required this drying step can further be accelerated by for example exposure to a stream of hot (dry) air. The test results can then reliably be established for quite a long period of time. This is especially of advantage when the apparatus described in the present invention is used for detection of pregnancy.

The holding device advantageously contains spacers between the cover and the base. These spacers ensure an adequate ventilation of the test strip. In addition the holding device is provided with a number of supporting elements for the test strip. Preferably the base is provided with lateral webs, which are constructed in such a way that a split is formed between the cover and the webs. This split guarantees an adequate ventilation of the test strip, but prevents, because of its narrow form that the test strip is touched upon by accident. The lateral webs and the cover extend over the entire length of the holding device. The spacers can, however, also be present at short distances only on the longitudinal or transverse sides. Spacers, supporting elements and lateral webs are advantageously made from the same material as the holding device.

The holding device contains at least one window through which the test result can be read. The window is, for example, a hole or a transparent section of the holding device. When the analytical system is designed in such a way that the presence of the specifically reacting substance is indicated by a colour, which is fixed at a certain spot of the test strip, the holding device contains at least one window through which this spot can be observed. Preferably the holding device contains additional windows at the place of control spots, which are included to garantee a correct test performance. The latter is of special importance when the apparatus is used by the layman for example to detect pregnancy.

The test strip advantageously consists of a material which transports the test liquid essentially by capillary forces. Advantageously absorbent, porous or fibrous material is used, which is suitable for rapid uptake of liquid. Suitable materials involve amorphous spong-like structures or various porous synthetic materials such as polypropylene, polyethylene, polyvinylidene fluoride, ethylene/vinyl acetate copolymer, polyacrylonitrile and polytetrafluoroethylene. In addition certain materials with an inherent hydrophobicity can also be pretreated with surface-active agents to such an extent that they are able to take up a test liquid and transport it by capillary forces. Other suitable materials include multilayer materials and materials which are already generally used in analytical test strips such as paper or paper-like materials, for example nitrocellulose.

The test strip can either be held in a flat position in the holding device or can at one end be bend and extended into the interior space of the housing. The latter construction facilitates the contact between test strip and test liquid.

Preferably the holding device comprises also an absorber, which is located downstream adjacent to the test strip, to remove excess test liquid. The material of the absorber is not critical and can be any material that is capable of absorbing liquids, for example a paper-like material or those materials which are mentioned for use as absorbing material in the sample collector.

Advantageously the test strip can be extended so that the strip itself can function as an absorber. In the latter case no additional absorber is needed. In order to gain space this extended test strip can be rolled or zigzag-folded.

Besides the absorber the holding device might contain a moisture-absorbing agent, such as silica, to guarantee a better stability of the analytical system on the test strip.

In one preferred embodiment of the invention the holding device can be separated from the housing. This makes the apparatus and especially the production of this apparatus more flexible, as the housing and holding device can be produced separately before assembling, while also different combinations of housing and holding device can be realized.

In another preferred embodiment of the invention the housing is an elongate housing, the holding device is located on the housing and the housing has a first opening for introducing the test liquid into the interior space, and a second opening which is located at a certain distance from the first opening and through which the test liquid can contact the test strip. The elongate housing enables the use of an elongate sample collector, which, in combination of the further special features regarding handling and reading, makes this embodiment especially suited for home-use detection of pregnancy.

In another preferred embodiment of the invention said elongated housing is provided with means to facilitate the contact with the test strip. These means can preferably be formed by an elevation on the inside wall of the housing, so that when a sample collector is introduced into the housing the tip of the sample collector is diverted and pressed against the test strip. The elevation is advantageously located at a position opposite the place where contact between the sample collector, containing the test liquid, and the test strip takes place.

The present invention also provides a sample collector comprising a handle and absorbing material which absorbs the test liquid rapidly and is capable of an easy direct or indirect release of test liquid to the test strip, whereby said sample collector can be introduced through the opening of the housing into the interior space of the apparatus according to the present invention. Transfer of the liquid sample from the sample collector to the test strip can be achieved by simply pressing. This transfer can be facilitated by special means in the housing, such as an elevation on the inner wall, or by bending the top end of the tests strip so that it extends into the interior space of the housing.

Instead of direct transfer of test liquid from the sample collector to the test strip, this transfer can also be realized in an indirect way by means of a connector. This connector transfers the test liquid from the sample collector to the test strip by capillary action. The connector can be made from the same material as that of the sample collector, but preferably with another, smaller, pore size. The connector can be fitted in various ways and can for example be located against the test strip or pressed aginst the test strip by the sample collector.

The sample collector comprises a material which can readily absorb test liquid, but also easily release this test liquid for example under mechanical pressure or capillary transfer. It can thus be a sponge-like material such as, for example, cotton wool or hydrophilic and hydrophilized synthetic polymer materials, such as polyethylene vinylacetate, as well as other polyesters, and polypropylene. To this material reagents can be added as, for example, buffering compounds to adjust the pH of the test liquid, or compounds able to eliminate possibly interfering substances present in the test liquid.

Another example of a sample collector comprises material that as such is not able to absorb and release test liquid, but is able to do so merely by its shape or construction.

Next to the absorbing material the sample collector comprises a handle, which can for example be provided with a colour. This colour can serve for sample identification and thus facilitate handling of larger numbers of different samples.

In another embodiment of the present invention the sample collector is provided with a connecting rod between the handle and the absorbing material, which facilitates handling of the sample collector. Between the rod and the handle a shoulder is provided on which the housing can rest on introduction of the sample connector.

The present invention is further directed to a device comprising the apparatus and sample collector described above, as well as to a method for the detection of at least one specifically reacting substance in a test liquid, whereby the above mentioned device is used.

There are no special restrictions with respect to the analytical test system on the test strip. An example of an analytical system is described in German Utility Model DE-U-88 05 565.5. Other variants are to be found in EP-A-0 183 442, WO-A-91/12528, EP-A-0 349 215 and EP-A-0 186 799. In a preferred embodiment, the term "analytical system" used herein indicates that a specific reactant (for example an antibody) forms a complex with the specifically reacting substance (for example the pregnancy hormone hCG) in a reaction (for example an immunological reaction). This complex is then (if it does not already carry a visible label) provided with a label, for example in a reaction with a labelled anti-antibody (this is a second antibody raised against immunoglobulins in general and therefore able to bind the hCG antibodies as well). The labelled complex can then be fixed and made visible at another point on the test strip via a reaction with another reagent immobilized on the test strip.

Although in principle all kinds of labels can be used, a preferred label for use in the present apparatus according to the invention is a so-called particulate label. Most preferably a direct particulate label is used, which gives a direct visible test result without the need for additional reagents or equipment. Said direct particulate label comprises small coloured particles, such as gold sol particles, latex particles, dyestuff particles, liposomes including a dye, carbon- and selenium sol particles etc. These particles are as such insoluble in water, but resuspendible in solution. All these particulate labels are well known in the literature (see Clin. Chem. 27, 1157, 1981, EP 007 654, EP 032 270, EP 291 194, EP 154 749, EP 321 008).

Gold sol particles are particularly advantageous. The gold sol particles advantageously have a diameter of about 5 to 100 nm in size.

The various reagents of the analytical system are distributed over various zones of the test strip, and a test liquid can then diffuse through them. A suitable pregnancy test strip (when gold particles are used as direct particulate labels) has the following zones (from upstream to downstream):
1st zone: antibodies against the pregnancy hormone hCG, labelled with gold sol particles, which are freely movable in the test strip after contact with a test liquid.
2nd zone: antibodies against hCG which are immobilized on the test strip.

In the first zone of this test strip an immunological reaction takes place between the freely movable gold sol-labelled hCG antibodies and any hCG present in the test liquid. The gold sol-labelled hCG antibody/hCG complex formed diffuses into the second zone. This complex is then bound to the immobilized hCG antibodies. Gold sol-labelled hCG antibodies which are not bound to hCG diffuse freely out of this second zone.

Another suitable pregnancy test strip comprises:
1st zone: gold sol-labelled hCG antibodies (freely movable).
2nd zone: hCG antibodies coupled to biotin (freely movable).
3rd zone: avidin (immobilized).

In the first zone any hCG present in the test liquid reacts with the gold sol-labelled hCG antibodies. The gold sol-labelled hCG antibody/hCG complex formed diffuses into the second zone where a "sandwich" complex is formed (gold sol-labelled hCG antibody/hCG/biotinylated hCG antibody). This "sandwich" complex then diffuses into the third zone where it is fixed by the very strong avidin/biotin interaction. The freely movable gold sol-labelled hCG antibodies which have not been complexed again diffuse freely out of this zone.

A particularly preferred test strip has the following zones:
1st zone: hCG antibodies (freely movable)
2nd zone: gold sol-labelled anti-antibodies (freely movable), which do not react immunologically with the hCG antibodies from the third zone.
3rd zone: hCG antibodies (immobilized).

In the first zone any hCG present in the test liquid forms in the first zone an hCG antibody/hCG complex. This complex diffuses into the second zone and reacts with the gold sol labelled anti-antibodies. The gold sol-labelled anti-antibody/hCG antibody/hCG complex then diffuses into the third zone, where it is fixed by the immobilized hCG antibody and where it can be detected visually. Complexes which contain no hCG (gold sol-labelled anti-antibody/hCG antibody complexes) are not bound in this zone and diffuse out of it.

The above analytical system on the test strip is preferred for various reasons:

a) This system guarantees a high affinity and specificity of the hCG antibodies in the first zone, where the primary reaction takes place with any hCG present in the test liquid, as these antibodies are present in their "natural" form. This means that they are not bound to a labelled compound nor immobilized onto the solid phase. Therefore the special characteristics of these antibodies such as a high affinity and specificity, which may be impaired by said binding reactions, are retained.

b) Some agglutination (complex formation) will occur between the specific hCG antibodies from the first zone and the gold sol-labelled anti-antibodies from the second zone. These complexes will then be transported to the third zone and, when they contain hCG, be fixed by the immobilized hCG antibodies from the third zone. These "agglutinated" complexes will contain more gold sol-labelled anti-antibodies than the hCG antibody/anti-antibody complexes which have not agglutinated. Therefore a higher amount of label is bound per hCG molecule, which means more colour and thus a higher sensitivity. This phenemenon is not shown for the other analytical systems.

c) Finally, the hCG antibodies from the first zone also act as "spacer" between the hCG in the test fluid and the gold sol-labelled anti-antibodies from the second zone. The distance between the label and the hCG is therefore larger. The hCG/hCG antibody/gold sol-labelled anti-antibody complex will therefore more easily bind to the immobilized hCG antibodies from the third zone, as there is less steric hindrance from the labelled antibodies. This also results in a higher sensitivity.

The reagents can be introduced onto the test strip in a variety of ways. For example, it is possible to use printing processes known per se for this purpose. In this case, the reagents may either merely be applied to the surface of the test strip or impregnated into the test strip. It is sometimes also advantageous to introduce the reagents in a microencapsulated form. This may be desirable when a reagent is required for fixation of the above mentioned labelled complexes, which interferes with the unbound labelled antibodies.

The binding reagents such as antibodies or avidin can be immobilized onto the test strip by covalent binding or absorption. These reagents can be immobilized as such or bound to particles, as for example latex particles.

If the test strip consists, for example, of nitrocellulose, the antibodies can be coupled directly without a previous chemical treatment of the test strip. After coupling, however, the remaining binding sites on the test strip should be blocked with, for example, treatment with hydrophilic synthetic polymers, such as polyvinylalcohol, or hydrophylic biopolymers, such as human and bovine serum albumin, ovalbumin and the like. If the test strip consists of other materials such as paper, covalent coupling can be achieved with CNBr or carbonyldiimidazole.

The test strip has preferably also a control zone which generates a colour signal irrespective of whether the sample contains the substance to be determined or not. Such a control zone contains, for example a colour coupler which reacts with the urea in the woman's urine. Alternatively, this control zone contains immobilized antibodies, anti-antibodies or other binding reagents which react with the labelled antibodies or labelled anti-antibodies.

Exemplary embodiments of the invention are explained in detail hereinafter.

BRIEF DESCRIPTION OF THE DRAWINGS

FIG. 1 and 2 show a plan view and side view respectively of an embodiment of the apparatus described in the present invention;

FIG. 3 and 4 show a cross-section and an axial section of the embodiment shown in FIG. 1;

FIG. 5 shows a plan view of a sample connector provided with a connecting rod, which can be used in the embodiment shown in FIG. 1–4;

FIG. 8 shows a plan view of a further embodiment of the invention;

FIGS. 9, 10, 11 illustrate a side view, a cross-section and an axial section respectively of the embodiment shown in FIG. 8;

FIG. 12 shows a plan view of a sample collector which can be used in the embodiment shown in FIG. 8;

FIGS. 14, 15, 16, 17 show a plan view, a side view, an cross-section and an axial section respectively of another embodiment of the invention, wherein a connector is used;

DESCRIPTION OF THE PREFERRED EMBODIMENT

Figure 6:
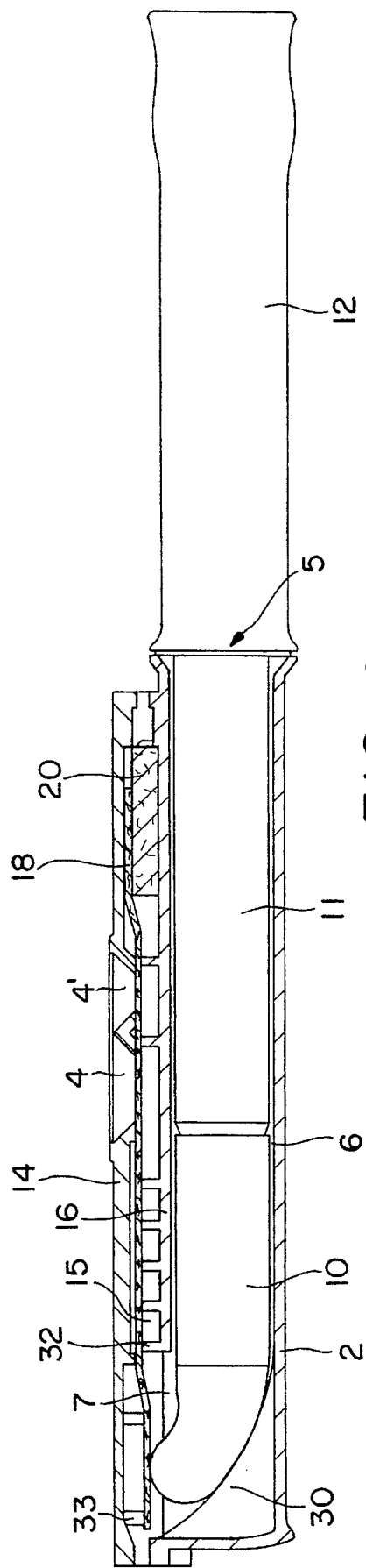
FIG. 6 shows an axial section of another embodiment including a sample collector.

The apparatus of FIG. 1–4 comprises a housing 2 as well as a holding device 3 in which a test strip 18 and an absorber 20 is held. The housing 2 has an opening 5 for introducing a test liquid, which may contain the substance to be analyzed, into the interior space 6 of the housing 2. The test liquid is introduced with a sample collector, comprising a handle 12, an absorbing material 10 a connecting rod 11 and a shoulder 13. The housing further contains an opening 7 via which contact of the test liquid with the test strip can take place. Contact between the sample collector and the test strip is facilitated by the elevation 30 on the inner wall of the housing 2, which presses the sample collector against the test strip 18. The holding device 3 comprises a cover 14, spacers 15, a base 16 and lateral webs 17 on which the cover, supported by the spacers, rests.

The lateral webs 17 are constructed in such a way that a split 19 is formed between the cover 14 and the lateral webs 17.

The holding device 3 contains one or more windows 4 and 4' through which the test result, preferably indicated by a colour on a certain spot of the test strip, can be observed.

FIG. 5 shows the sample collector used in the apparatus of FIGS. 1–4.

FIG. 6 shows another embodiment of the apparatus according to the present invention, including a sample collector, wherein the test strip 18 is held in position by the supporting elements 32 and 33.

Figure 7:
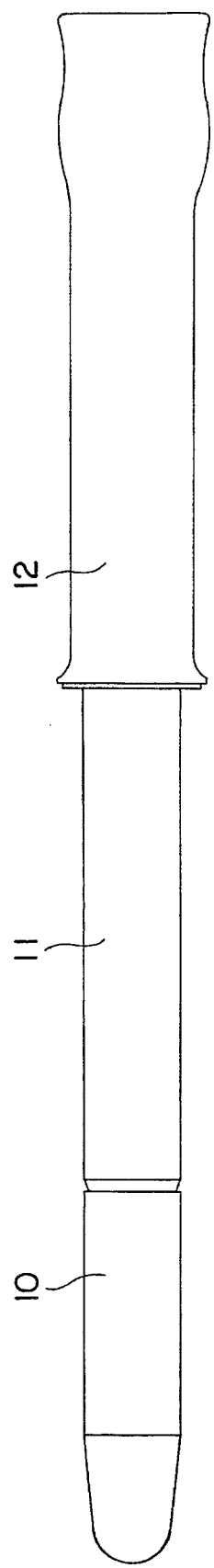
FIG. 7 shows a plan view of a sample collector which can be used in the embodiment shown in FIG. 6.

FIG. 7 shows the sample collector used in the apparatus of FIG. 6.

FIGS. 8–11 show a further embodiment of the apparatus according to the present invention, wherein the test strip 18 is bend and extended into the interior space 6 of the housing 2 to facilitate the contact between the sample collector with the absorbing material 10 and the test strip 18.

FIG. 12 shows the sample collector used in the apparatus of FIGS. 8–11.

Figure 13:
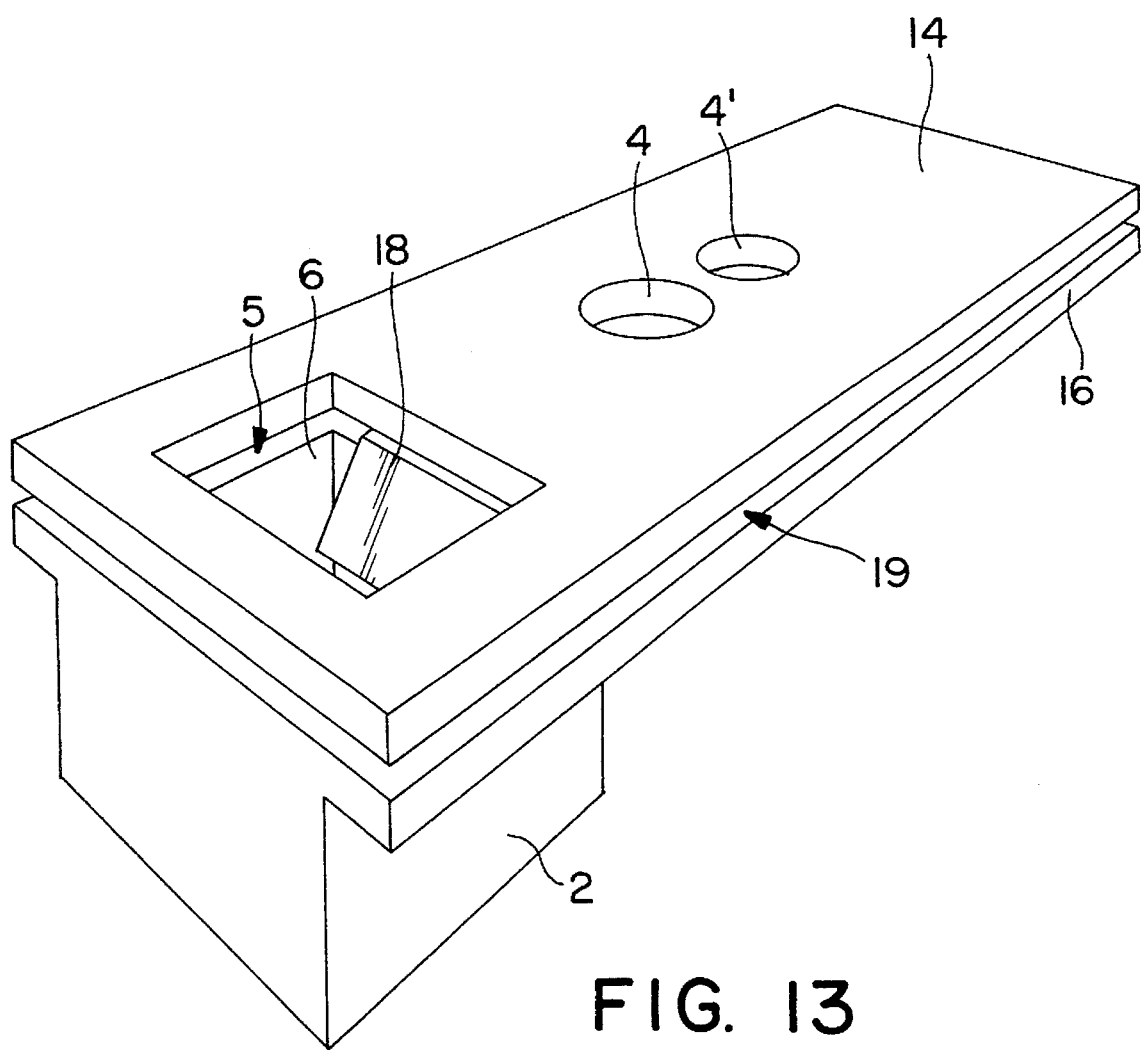
FIG. 13 shows a plan view of another embodiment of the invention.
Figure 16:
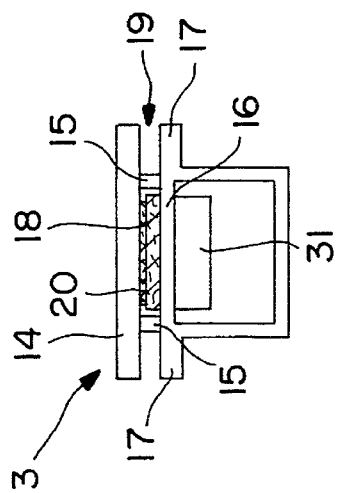
Figure 17:
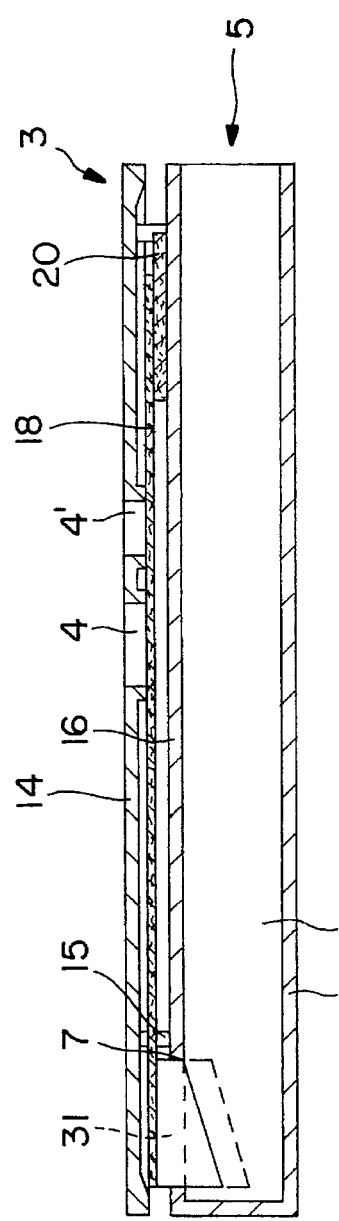
Figure 18:
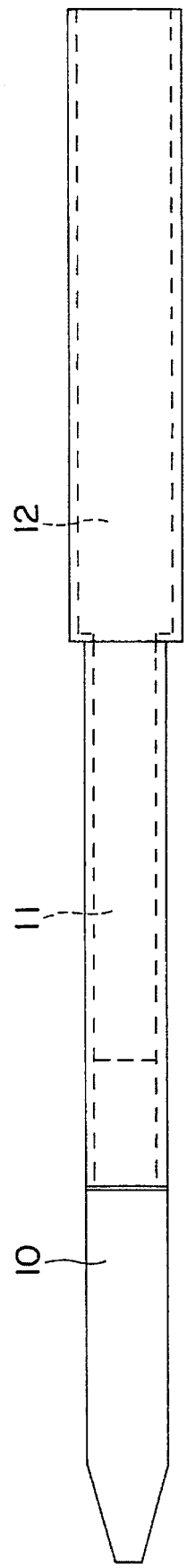
FIG. 18 shows a sample collector which can be used in the embodiment shown in FIGS. 14–17.

FIG. 13 shows another embodiment of the apparatus according to the invention, whereby the test strip 18 is extending into the interior space 6 of the housing 2 and the test liquid is introduced via the opening 5.

FIGS. 14–17 show another embodiment of the apparatus described in the present invention, wherein contact between sample collector and test strip is made via a connector 31.

Detection of, for example, hCG with the apparatus according to the present invention, whereby the analytical system comprises a first zone with hCG antibodies, a second zone with labelled anti-antibodies and a third zone with immobilized hCG antibodies, can be carried out as follows:

A test liquid, which may contain hCG, is introduced, either directly or indirectly by means of a sample collector, into the interior space of the housing of the apparatus according to the present invention. This sample collector, comprising an absorbing material, gets in contact with the test strip comprising the analytical system, when it is introduced into the housing. The test liquid is released and transported through the test strip by capillary action. Any hCG which is present in the test liquid, reacts with the specific hCG antibodies from the first zone. The hCG antibody/hCG complex formed is then transported with the test liquid into the second zone, where it reacts with the anti-antibodies labelled with gold sol particles. The complex obtained in this way is transported into a third zone, where it is fixed by the immobilized hCG antibodies from the third zone. The hCG present in the test liquid can then detected by reading the colour at this fixation spot in the third zone. Furthermore the test performance is controlled by observing the colour at the control spot in the fourth zone, which always should give a positive result.

The present invention will now be further particularly described with reference to the following Examples. The apparatus used is that depicted in FIG. 6.

EXAMPLE 1

1. Preparation of gold sol labelled monoclonal rat anti-mouse IgG (gold sol conjugate)

Gold sols with an average particle diameter of 50 nm ($A_{540}$=5.0) were prepared according to the method described by Frens (Nature Physical Science Vol. 240, 1973, 20).

A solution of 1 mg monoclonal rat anti-mouse IgG (anti-kappa) per ml sodium chloride (9 g/l) was adjusted to pH 8.0 using 0.1M sodium hydroxide. 1 l of the gold sol solution was adjusted to pH 8.0 with 0.1M sodium hydroxide, mixed with 20 ml of the monoclonal rat anti-mouse IgG solution and subsequently postcoated by adding 40 ml of a 20M polyethylene glycol solution, pH 8.0. The postcoated gold sol conjugate was sedimented by centrigugation for 20 min. at 3500 g at ambient temperature. After removing the supernatant by suction the gold sol conjugate pellet was resuspended to an $A_{540}$ value of 50.0 in a solution containing 2% (v/v) foetal calf serum, 160 g/l sucrose, 2% (w/v) Triton X100 and 1M Tris, pH 8.0.

2. Preparation of a monoclonal anti-hCG IgG solution

Monoclonal hCG antibodies (beta-subunit specific) were prepared essentially as described in EP 045 103. 40 g of monoclonal anti-hCG IgG was dissolved in 1 l of a solution containing 1M Tris, pH 8.0, 160 g/l sucrose and 2% (w/v) Triton X100.

3. Preparation of polyclonal anti-hCG IgG

Polyclonal antibodies against hCG were prepared according to conventional techniques. 6 g of immunopurified anti-hCG IgG were dissolved in 1 l of a solution containing 3.5 mM Tris, pH 8.0, and 9 g/l sodium chloride.

4. Preparation of test strips

On a rectangular sheet of glass paper measuring 100 mm in length and 70 mm in width a first mobile reaction zone was formed by applying, along the width, a solution of monoclonal anti-hCG IgG (see under 2), in a line 5 mm wide and 10 mm from the bottom edge of the glass paper sheet.

A second mobile reaction zone was formed on the same glass paper sheet by applying, again along the width, a solution of gold sol conjugate (see under 1), in a line 5 mm wide and 16 mm from the edge of the glass paper sheet. Both mobile reaction zones were air dried (50° C.) and the sheet was cut along its length to strips which were 7 mm wide.

A third reaction zone (detection zone) was formed on each test strip by pipetting, 40 mm from the bottom edge, 1 μl of a solution of polyclonal hCG IgG (see under 3).

A fourth reaction zone (control zone) was formed on each test strip by pipetting, 50 mm from the bottom edge, 1 μl of the monoclonal anti-hCG IgG solution (see under 2).

The detection and control zones were subsequently air-dried (50° C.).

5. Assembly and testing of the apparatus

Test strips were assembled in an apparatus as described in the present invention and tested with urines from non-pregnant women spiked with various concentrations of hCG (15–25–300 000 IU/l). In addition an hLH standard was tested in a concentration of 500 IU/l. 4 min. after insertion of the apparatus into the urine sample the following results were observed:

|            | detection zone | control zone |
|------------|----------------|--------------|
| hCG (IU/l) |                |              |
| 0          | –              | +            |
| 15         | +/–            | +            |
| 25         | +              | +            |
| 300 000    | +              | +            |
| hLH (IU/l) |                |              |
| 500        | –              | +            |

EXAMPLE 2

1. Preparation of carbon sol labelled monoclonal anti-hCG IgG (carbon sol conjugate)

0.5 g of Degussa Spezial Schwarz 100 was suspended in 50 ml 5 mM borate buffer with a pH of 8.6.

This suspension was sonified (27 W, 20 kHz; Branson Sonifier) during 30 min. under stirring and cooling on ice. This 1% C-sol can be kept at ambient temperature.

A suspension was made of 10 ml 1% C-sol in 40 ml 5 mM borate buffer, pH 8.6. This suspension was proceeded further as indicated above for the 1% C-sols. The resulting 0.2% C-sol can be kept at ambient temperature.

A solution of 1 mg monoclonal anti-hCG IgG (beta-subunit specific; see Example 1) per ml sodium chloride (9 g/l) was adjusted to pH 8.0 using 0.1M sodium hydroxide.

1 l of the carbon sol solution was adjusted to pH 8.6 with 5 mM boric acid, mixed with 20 ml of the monoclonal anti-hCG solution and incubated under stirring for 2 hours at ambient temperature.

Subsequently the carbon sol conjugate was sedimented by centrifugation for 6 min. at 10 000 g at ambient temperature. After removing the supernatant by suction, the carbon pellet was resuspended to a volume of 1 l in a solution containing 2% (v/v) foetal calf serum, 160 g/l sucrose, 2% (w/v) Triton X100 and 1M Tris, pH 8.6.

2. Preparation of a monoclonal anti-hCG IgG solution

Monoclonal hCG antibodies (alpha-subunit specific) were prepared essentially as described in EP 045 103.3 g of monoclonal anti-hCG IgG was dissolved in 1 l of a solution containing 25 mM Tris, pH 8.0, and 9 g/l sodium chloride.

3. Preparation of a monoclonal rat anti-mouse IgG solution 3 g of monoclonal rat anti-mouse IgG (anti-kappa) was dissolved in 1 l of a solution containing 25 mM Tris, pH 8.0, and 9 g/l sodium chloride.

4. Preparation of test strips

On a rectangular sheet of glass paper (100 mm in length and 70 mm in width) a mobile reaction zone was formed by applying along the width, a solution of carbon sol conjugate (see under 1), in a line 5 mm wide and 10 mm from the bottom edge of the glass paper sheet. The mobile reaction zone was air dried (50° C.) and the sheet was cut along its length to strips which were 7 mm wide.

A second reaction zone (detection zone) was formed on each test strip by pipetting, 40 mm from the bottom edge, 1 μl of the monoclonal anti-hCG IgG solution (see under 2).

A third reaction zone (control zone) was formed on each strip by pipetting, 50 mm from the bottom edge, 1 μl of the monoclonal rat anti-mouse IgG solution (see under 3).

5. Assembly and testing of the apparatus

Test strips were assembled in an apparatus as described in the present invention and tested with urines from non-pregnant women spiked with various concentrations of hCG (10–25–300 000 IU/l). In addition an hLH standard was tested in a concentration of 500 IU/l.

2 min. after insertion of the apparatus into the urine sample the following results were observed:

|  | detection zone | control zone |
|---|---|---|
| hCG (IU/l) | | |
| 0 | − | + |
| 15 | + | + |
| 25 | + | + |
| 300 000 | + | + |
| hLH (IU/l) | | |
| 500 | − | + |

We claim:

1. Apparatus for the detection of at least one substance in a test liquid comprising:
   a housing,
   a holding device, and
   a test strip which is held in the holding device and which includes a material that transports the test liquid essentially by capillary forces and comprises an analytical system which indicates the presence or absence of said substance to be detected, wherein the housing has an interior space and a first opening for introducing said test liquid into said interior space,
   wherein said holding device is held on said housing with a gap along at least one side of said holding device for allowing evaporation of test liquid and said holding device being provided with at least one window for observing the indication of the presence or absence of said substance to be detected.

2. The apparatus according to claim 1, wherein the holding device is detachable from the housing.

3. The apparatus of claim 1, wherein the analytical system is a colormetric system.

4. The apparatus of claim 1, further comprising contact means for allowing contact of the test liquid with the test strip.

5. Method for the detection of at least one specifically reacting substance in a test liquid, whereby the device according to claim 1 is used.

6. Method according to claim 5, whereby the specifically reacting substance is hCG or hLH.

7. The apparatus according to claim 1, wherein said at least one window of said holding device allows for observation of a first side of said test strip, and wherein said gap along said at least one side of said holding device exposes an opposite side of said test strip to airflow across said test strip.

8. The apparatus of claim 7, wherein said test strip and said holding device are elongated with longitudinal and transverse sides, and wherein said at least one gap is a gap between said housing and, respectively, each of said longitudinal sides of said holding device, so as to allow airflow across said test strip via said longitudinal gaps.

9. The apparatus of claim 8, wherein said at least one gap is a gap between each of said longitudinal and transverse sides and said housing.

10. The apparatus of claim 1, wherein said labelled compound is a freely mobile labelled reactant for said at least one substance in the test liquid.

11. The apparatus of claim 10, wherein said analytical system further comprises an immobilized reagent for said at least one substance.

12. The apparatus of claim 11, wherein said labelled compound is an antibody against pregnancy hormone hCG labelled with gold sol particles, and said immobilized reagent is an antibody against hCG immobilized on the test strip.

* * * * *